US006685922B2

(12) United States Patent
Peterson

(10) Patent No.: US 6,685,922 B2
(45) Date of Patent: Feb. 3, 2004

(54) TOOTH WHITENING MATERIAL AND METHOD OF WHITENING TEETH

(75) Inventor: Kenneth S. Peterson, Lancaster, PA (US)

(73) Assignee: Dentsply International Inc.

( * ) Notice: Subject to any disclaimer, the term of this patent is extended or adjusted under 35 U.S.C. 154(b) by 0 days.

(21) Appl. No.: 09/815,866

(22) Filed: Mar. 23, 2001

(65) Prior Publication Data

US 2003/0012747 A1 Jan. 16, 2003

Related U.S. Application Data

(60) Provisional application No. 60/191,588, filed on Mar. 23, 2000.

(51) Int. Cl.$^7$ .................................................. A61K 7/20
(52) U.S. Cl. ........................ 424/53; 433/215; 433/216; 433/228.1
(58) Field of Search ........................ 424/53, 215, 211, 424/228.1

(56) References Cited

U.S. PATENT DOCUMENTS

| | | | | |
|---|---|---|---|---|
| 1,934,688 | A | 11/1933 | Ackerman | 32/5 |
| 2,257,709 | A | 9/1941 | Anderson | 128/260 |
| 2,684,924 | A | 7/1954 | Rose et al. | 167/30 |
| 2,835,628 | A | 5/1958 | Saffir | 167/84 |
| 2,863,919 | A | 12/1958 | Birtwell et al. | 260/565 |
| 2,930,006 | A | 3/1960 | Hathaway | 333/71 |
| 3,010,705 | A | 11/1961 | Brown | 259/98 |
| 3,060,935 | A | 10/1962 | Riddell | 128/260 |
| 3,073,300 | A | 1/1963 | Berghash | 128/136 |
| 3,234,942 | A | 2/1966 | Simor | 128/172.1 |
| 3,247,844 | A | 4/1966 | Berghash | 128/136 |
| 3,379,193 | A | 4/1968 | Monagham | 128/136 |
| 3,380,446 | A | 4/1968 | Martin | 128/24 |
| 3,385,291 | A | 5/1968 | Martin | 128/62 |
| 3,416,527 | A | 12/1968 | Hoef | 128/260 |
| 3,448,738 | A | 6/1969 | Berghash | 128/136 |
| 3,481,329 | A | 12/1969 | Warren | 128/66 |
| 3,499,844 | A | 3/1970 | Kibbel et al. | 252/316 |
| 3,526,069 | A | 9/1970 | Deike | 52/160 |
| 3,527,219 | A | 9/1970 | Greenberg | 128/260 |
| 3,624,909 | A | 12/1971 | Greemberg | 32/40 |
| 3,625,215 | A | 12/1971 | Quisling | 128/260 |
| 3,657,413 | A | 4/1972 | Rosenthal | 424/81 |
| 3,700,215 | A | 10/1972 | Hardman et al. | 259/98 |
| 3,742,942 | A | 7/1973 | Westline | 128/62 |
| 3,844,286 | A | 10/1974 | Cowen | 128/260 |
| 3,955,281 | A | 5/1976 | Weitzman | 32/14 B |
| 3,969,499 | A | 7/1976 | Lee, Jr. et al. | 424/52 |
| 3,988,433 | A | 10/1976 | Benedict | 424/53 |
| 3,998,945 | A | 12/1976 | Vit | 424/53 |
| 4,032,627 | A | 6/1977 | Suchan et al. | 424/54 |
| 4,044,762 | A | 8/1977 | Jacobs | 128/136 |
| 4,060,082 | A | 11/1977 | Lindberg et al. | 128/218 M |
| 4,064,628 | A | 12/1977 | Weitzman | 32/14 B |
| 4,138,814 | A | 2/1979 | Weitzman | 32/14 B |
| 4,164,940 | A | 8/1979 | Quinby | 128/62 A |
| 4,172,457 | A | 10/1979 | Choksi | 128/272.1 |
| 4,173,219 | A | 11/1979 | Lentine | 128/260 |
| 4,173,505 | A | 11/1979 | Jacobs | 156/285 |
| 4,183,916 | A | 1/1980 | Rodon | 424/54 |
| 4,251,507 | A | 2/1981 | Olson | 424/49 |
| 4,302,441 | A | 11/1981 | Muhlemann | 424/48 |
| 4,359,049 | A | 11/1982 | Redl et al. | 128/218 PA |
| 4,376,628 | A | 3/1983 | Aardse | 433/80 |
| 4,428,373 | A | 1/1984 | Seid et al. | 604/77 |
| 4,431,631 | A | 2/1984 | Clipper et al. | 424/53 |
| 4,464,174 | A | 8/1984 | Ennis | 604/90 |
| 4,516,967 | A | 5/1985 | Kopfer | 604/87 |
| 4,518,721 | A | 5/1985 | Dhabhar et al. | 523/120 |
| 4,522,805 | A | 6/1985 | Gordon | 424/52 |
| 4,528,180 | A | 7/1985 | Schaeffer | 424/52 |
| 4,537,778 | A | 8/1985 | Clipper | 424/53 |
| 4,538,920 | A | 9/1985 | Drake | 366/177 |
| 4,551,135 | A | 11/1985 | Gorman et al. | 604/82 |
| 4,560,351 | A | 12/1985 | Osborne | 433/80 |
| 4,568,536 | A | 2/1986 | Kronenthal et al. | 424/22 |
| 4,592,487 | A | 6/1986 | Simom et al. | 222/94 |
| 4,592,488 | A | 6/1986 | Simon et al. | 222/94 |
| D287,877 | S | 1/1987 | Holewinski et al. | D24/14 |
| 4,661,070 | A | 4/1987 | Friedman | 433/203.1 |
| 4,687,663 | A | 8/1987 | Schaeffer | 424/52 |
| 4,696,757 | A | 9/1987 | Blank et al. | 252/186.29 |
| D294,640 | S | 3/1988 | Wicken et al. | D24/60 |
| 4,743,229 | A | 5/1988 | Chu | 604/82 |
| 4,770,634 | A | 9/1988 | Pellico | 433/217.1 |
| 4,788,052 | A | 11/1988 | Ng et al. | 424/53 |
| D300,349 | S | 3/1989 | Ennis, III | D24/231 |
| 4,812,308 | A | 3/1989 | Winston et al. | 424/52 |
| 4,839,156 | A | 6/1989 | Ng et al. | 424/53 |
| 4,839,157 | A | 6/1989 | Mei-King Ng et al. | 424/53 |
| 4,849,213 | A | 7/1989 | Schaeffer | 424/53 |
| D302,726 | S | 8/1989 | Schwobel | D24/24 |
| D303,427 | S | 9/1989 | Shimp et al. | D24/14 |
| 4,886,658 | A | 12/1989 | Charbonneau et al. | 424/53 |
| 4,895,721 | A | 1/1990 | Drucker | 424/53 |
| D306,069 | S | 2/1990 | Kelly et al. | D24/24 |
| 4,902,227 | A | 2/1990 | Smith | 433/215 |
| 4,939,284 | A | 7/1990 | Degenhardt | 558/142 |
| D310,876 | S | 9/1990 | Jervis | D24/14 |
| 4,954,487 | A | 9/1990 | Cooper et al. | 514/159 |
| 4,961,923 | A | 10/1990 | Heyde | 424/49 |
| 4,968,251 | A | 11/1990 | Darnell | 433/216 |
| 4,971,782 | A | 11/1990 | Rudy et al. | 424/53 |

(List continued on next page.)

OTHER PUBLICATIONS

US 5,665,666, 9/1997, Fischer (withdrawn)

Primary Examiner—Shep K. Rose
(74) Attorney, Agent, or Firm—Douglas J. Hura; James B. Bieber

(57) ABSTRACT

A dental tooth whitening material sets to a rubber-like or elastomeric yet fluid consistency. The material includes hydrogen peroxide. A method of whitening teeth employs such a material by placing it into a dental tray or by placing the material directly onto a tooth. Once the material has set to its solid or semi-solid yet fluid consistency, the dental tray, if employed, can be left in place or removed.

1 Claim, 1 Drawing Sheet

U.S. PATENT DOCUMENTS

| | | |
|---|---|---|
| 4,980,152 A | 12/1990 | Frazier .......................... 424/52 |
| D313,470 S | 1/1991 | Talonn et al. ................ D24/24 |
| 4,983,379 A | 1/1991 | Schaeffer ..................... 424/52 |
| 4,983,381 A | 1/1991 | Torres Zaragoza ........... 424/53 |
| 4,988,500 A | 1/1991 | Hunter et al. ................. 424/53 |
| 4,990,089 A | 2/1991 | Munro ........................ 433/215 |
| 5,000,942 A | 3/1991 | Libin ........................... 424/53 |
| D316,600 S | 4/1991 | Austin, Jr. et al. ........... D24/14 |
| 5,032,178 A | 7/1991 | Cornell ......................... 106/35 |
| D321,759 S | 11/1991 | Buswell et al. ............ D24/130 |
| 5,084,268 A | 1/1992 | Thaler .......................... 424/53 |
| 5,098,303 A | 3/1992 | Fischer ....................... 433/215 |
| 5,110,583 A | 5/1992 | Sampathkumar ............. 424/48 |
| 5,122,365 A | 6/1992 | Murayama ................... 424/49 |
| D328,643 S | 8/1992 | Mitchell ..................... D24/114 |
| 5,165,424 A | 11/1992 | Silverman ................... 128/861 |
| 5,171,564 A | 12/1992 | Nathoo et al. ................ 424/53 |
| RE34,196 E | 3/1993 | Munro ........................ 433/215 |
| 5,208,010 A | 5/1993 | Thaler .......................... 424/53 |
| D338,957 S | 8/1993 | De Feire et al. ........... D24/130 |
| 5,234,342 A | 8/1993 | Fischer ....................... 433/215 |
| 5,240,415 A | 8/1993 | Haynie ....................... 433/216 |
| 5,256,402 A | 10/1993 | Prencipe et al. .............. 424/53 |
| 5,279,816 A | 1/1994 | Church et al. ................ 424/53 |
| 5,290,566 A | 3/1994 | Sckow et al. ................ 424/488 |
| 5,302,375 A | 4/1994 | Viscio .......................... 424/53 |
| 5,356,291 A | 10/1994 | Darnell ....................... 433/216 |
| 5,376,006 A | 12/1994 | Fischer ....................... 433/215 |
| 5,401,495 A | 3/1995 | Murayama ................... 424/49 |
| D357,065 S | 4/1995 | Castellini ................... D24/112 |
| 5,409,631 A | 4/1995 | Fischer ................. 252/186.25 |
| D359,560 S | 6/1995 | Mitchell .................... D24/176 |
| 5,425,580 A | 6/1995 | Beller ......................... 366/131 |
| D363,986 S | 11/1995 | Pena .......................... D24/114 |
| 5,472,422 A | 12/1995 | Ljungquist ................... 604/89 |
| D377,687 S | 1/1997 | Udovch ..................... D24/114 |
| 5,631,000 A | 5/1997 | Pellico et al. ................. 424/53 |
| 5,645,428 A | 7/1997 | Yarborough ................ 433/215 |
| 5,697,918 A | 12/1997 | Fischer et al. .............. 604/227 |
| 5,713,738 A | 2/1998 | Yarborough ................ 433/215 |
| 5,718,886 A | 2/1998 | Pellico ......................... 424/53 |
| 5,725,843 A | 3/1998 | Fischer ........................ 424/49 |
| 5,746,598 A | 5/1998 | Fischer ....................... 433/216 |
| 5,766,011 A | 6/1998 | Sibner ........................ 433/215 |
| 5,766,574 A | 6/1998 | Christina-Beck et al. ..... 424/53 |
| 5,770,105 A | 6/1998 | Fischer .................. 252/186.25 |
| 5,772,665 A | 6/1998 | Glad et al. ..................... 604/82 |
| D397,790 S | 9/1998 | Naganuma ................. D24/100 |
| 5,810,773 A | 9/1998 | Pesnicak ...................... 604/83 |
| D399,315 S | 10/1998 | Fulk et al. .................. D24/114 |
| 5,817,055 A | 10/1998 | Ljungquist ................... 604/89 |
| D401,324 S | 11/1998 | Hjertman et al. ........... D24/114 |
| D401,325 S | 11/1998 | Hjertman et al. ........... D24/114 |
| D403,064 S | 12/1998 | Einav et al. ................ D24/114 |
| 5,851,512 A | 12/1998 | Fischer ........................ 424/49 |
| 5,858,332 A | 1/1999 | Jensen et al. ................. 424/43 |
| 5,879,691 A | 3/1999 | Sagel et al. .................. 429/401 |
| 5,891,453 A | 4/1999 | Sagel et al. .................. 424/401 |
| 5,894,017 A | 4/1999 | Sagel et al. .................. 424/401 |
| D409,305 S | 5/1999 | Martin et al. .............. D24/113 |
| 5,902,568 A | 5/1999 | Ryles et al. ................... 424/53 |
| 5,908,054 A | 6/1999 | Safabash et al. .............. 141/26 |
| 5,922,307 A | 7/1999 | Montgomery ................ 424/53 |
| 5,928,628 A | 7/1999 | Pellico ......................... 424/49 |
| 5,944,528 A | 8/1999 | Montgomery ............... 433/215 |
| 5,945,032 A | 8/1999 | Breitenbach et al. .. 252/186.29 |
| 5,985,249 A | 11/1999 | Fischer ........................ 424/49 |
| 5,989,526 A | 11/1999 | Aaslyng et al. ............... 424/50 |
| 5,989,569 A | 11/1999 | Dirksing et al. ............. 424/401 |
| 6,004,538 A | 12/1999 | Hughes et al. ................ 424/49 |
| 6,045,811 A | 4/2000 | Dirksing et al. ............. 424/401 |
| 6,096,328 A | 8/2000 | Sagel et al. .................. 424/401 |

TOOTH WHITENING MATERIAL AND METHOD OF WHITENING TEETH

RELATED APPLICATION

This application which claims the benefit of U.S. Provisional Application Ser. No. 60/191,588 filed on Mar. 23, 2000.

FIELD OF THE INVENTION

The present invention relates to a two component dental bleaching system and method for bleaching human dentition. More particularly, the invention relates to tooth whitening material formed from a powder component and a liquid component, that sets to an elastomeric-like, semi-solid texture that also exhibits a fluid-like characteristic for placement into or onto a mouthpiece or other delivery medium for delivery to dentition or directly to dentition.

BACKGROUND OF THE INVENTION

This invention relates in general to teeth whitening materials used by a dental practitioner to whiten human teeth. For a variety of reasons it has become desirable for a person's teeth to appear bright or "white". Society places a high value on the "whiteness" of one's teeth.

A tooth is comprised of an inner dentin layer and an outer hard enamel layer that is the protective layer of the tooth. The enamel layer of a tooth is naturally an opaque white or slightly off-white color. It is this enamel layer that can become stained or discolored.

Many substances that a person confronts or comes in contact with on a daily basis can "stain" or reduce the "whiteness" of one's teeth. In particular, the foods, tobacco products and fluids that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth. Some pharmaceuticals, diseases and environmental factors may also have the effect of discoloring one's teeth. So long as the discolored teeth are still healthy and do not pose any health risk or problem, a product or substance that would whiten the discolored teeth would be advantageous.

It is known in the art to provide compositions containing hydrogen peroxide and to contact a patient's teeth with the composition. Prolonged contact will bleach and whiten stained teeth. Because many known peroxide compositions are viscous or even liquid, it has been a common practice to provide a dental tray molded to the patient's dentition to hold the bleaching material in place for sufficient time to effect bleaching. Without the tray, the bleaching material either flows away on its own or is degraded and removed by saliva.

Whitening compositions may be thought of as being of two types: in-office materials and take-home materials. Dental professionals may carry out the in-office treatment, while the take-home materials are designed to be administered by the patients themselves. As can be expected, the in-office treatments can be carried out using bleaching compositions having higher peroxide concentrations as compared to take-home materials. This is for the obvious safety reasons.

The dental bleaching systems heretofore known in the art have been effective in whitening teeth. However, there has been to date the requirement that the dental tray employed be closely configured to the dentition. Otherwise, the saliva effects noted above are compounded. An exemplary tooth whitening material employing a dental tray is shown for example in U.S. Pat. No. Re. 34,196, which is hereby incorporated by reference. It would be desirable however, to have a dental material that was not as dependent upon the use of a dental tray, or which in certain cases, not require a dental tray at all. A need exists therefore, for such an improved tooth whitening material.

BRIEF DISCLOSURE OF THE INVENTION

It is therefore, an object of the present invention to provide a tooth whitening composition.

It is another object of the invention to provide such a material that sets to at least a semi-solid and/or elastomeric texture.

It is still another object of the invention to provide a method of whitening teeth.

These and other objects of the invention, which will become apparent from the present disclosure, are carried out by the invention as herein described.

In general, a tooth whitening material comprises a solid or powder component and a liquid component. When mixed, the resulting composition will set to an elastomeric quality within about 1 to about 5 minutes. Exemplary powder components include mixed sodium/calcium salts of poly (methyl vinyl ether/maleic anhydride) and titanium dioxide. Liquid components include hydrogen peroxide in an amount of from about 30 to about 35 percent by weight, and water.

A method of bleaching teeth according to the invention includes preparing a mixture of a powder component and a liquid component. When mixed, the resulting composition will set to an elastomeric quality within about 1 to about 5 seconds. Exemplary powder components include mixed sodium/calcium salts of poly(methyl vinyl ether/maleic anhydride) and titanium dioxide. Liquid components include hydrogen peroxide in an amount of from about 30 to about 35 percent by weight, and water. This method may include placing the mixture into a dental tray and placing the tray onto the human dentition. The method may further include removing the tray after a period of time and after the mixture has set to an elastomeric texture, leaving the set mixture in place upon the human dentition.

Another method according to the present invention includes applying such a mixture to a tooth without the use of a dental tray.

PREFERRED EMBODIMENTS FOR CARRYING OUT THE INVENTION

Figure 1:
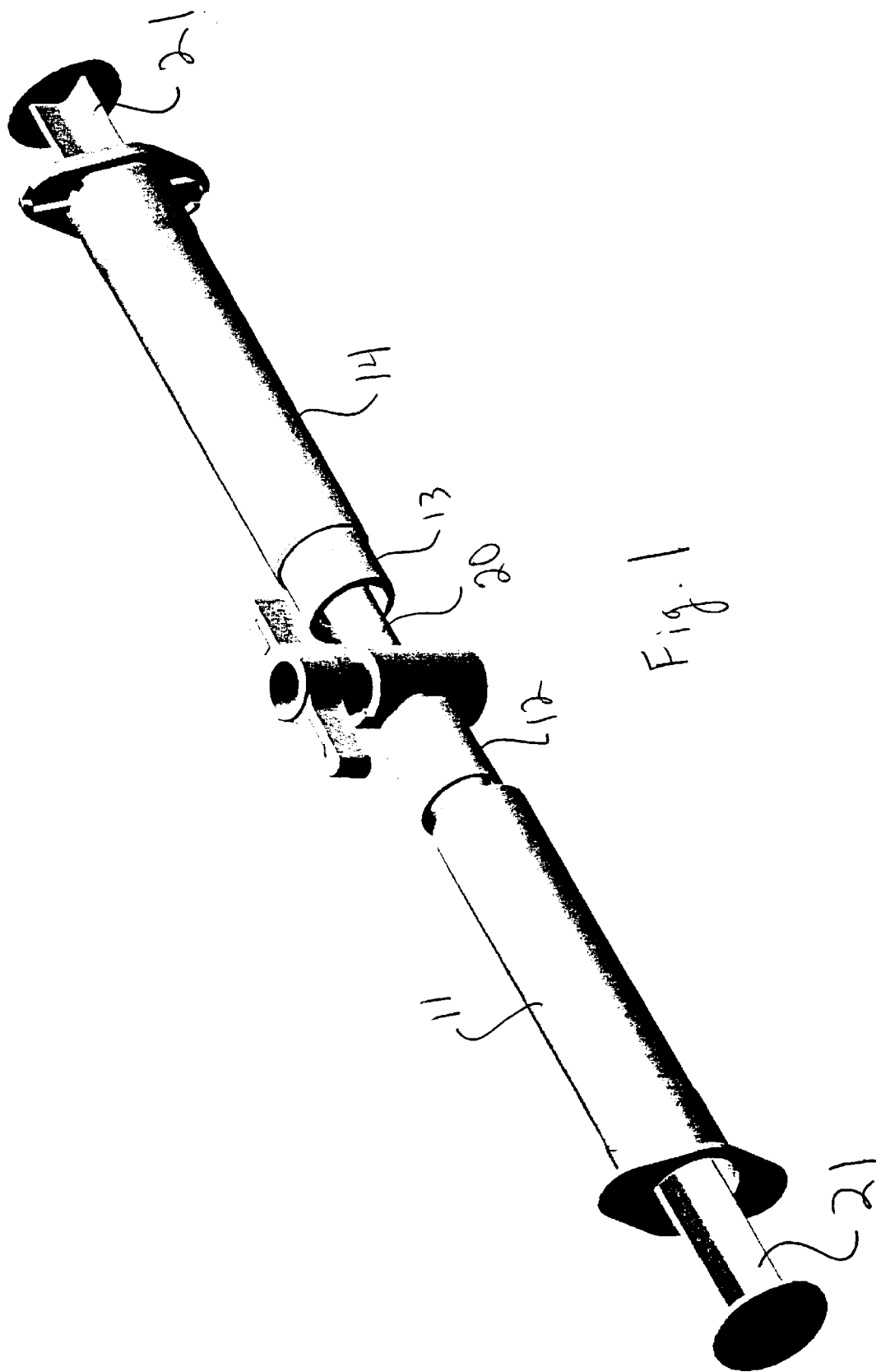
FIG. 1 is a perspective view of a dual syringe mixing apparatus suitable for use in the present invention to mix a powder component and a liquid component, and to then dispense the material as required.

The present invention provides a tooth whitening material which includes from about 10 to about 70 percent by weight of a hydrogen peroxide solution, preferably a hydrogen peroxide solution being about 3 to about 50 percent by weight of hydrogen peroxide and water; from 0 to about 40 percent by weight of carbamide peroxide, preferably being either 100 percent carbamide peroxide or at least 98 percent by weight carbamide peroxide and water; from about 0 to about 30 percent by weight glycerin, preferably from about 96 to about 99.8 percent by weight of glycerin and water;

from 0 to about 40 percent by weight of water, preferably purified water; from about 15 to about 65 percent by weight of a mixed powder of sodium/calcium salts of the copolymer of methyl vinyl ether/maleic anhydride or a blend of a mixed sodium/calcium salt of the copolymer of methyl vinyl ether/maleic anhydride; and from about 0 to about 10 percent by weight of titanium dioxide. In this composition, glycerin can be substituted with other polyols or hydrogenated starch solutions or the like. Further, titanium dioxide can be substituted with other filler agents such as silicon.

The present invention is preferably a two-component tooth whitening material that is intended to be used by a dental practitioner as opposed to being used by a non-professional patient. The material employs hydrogen peroxide in concentrations preferably of from about 30 to about 35 percent by weight. The material is prepackaged with a solid or powder component separate from a liquid component. The liquid component contains the hydrogen peroxide in water, and may contain other conventional components such as stabilizers, flavoring agents, or the like.

The liquid component may also comprise other conventional whitening agents such as carbamide peroxide, if desired.

The powder component preferably comprises mixed sodium/calcium salts of poly(methyl vinyl ether/maleic anhydride). Such a polymer is available for example from International Specialty Products as Gantrez. A particularly useful grade of Gantrez is Gantrez MS-955.

The two components, liquid and powder, are blended in ratios of from 20 to 80 parts by weight of hydrogen peroxide to 20 to 80 parts by weight of Gantrez. Preferably, the powder component is the Gantrez is mixed with titanium dioxide. Preferred Gantrez and titanium dioxide mixtures include 99:1 (Gantrez: titanium dioxide) to 90:10 by weight.

One preferred embodiment of the present invention includes from about 40 to about 60 parts by weight of hydrogen peroxide and from about 60 to about 40 parts by weight of a 99:1 Gantrez/titanium dioxide powder mixture. The two parts are blended together for about 10 to about 60 seconds, and the resultant mixture is a creamy white to off-white material. The material sets to an elastomeric or rubber-like, solid or semi-solid texture in from about 1 to about 5 minutes. Before setting, the material can be placed into a dental tray, or applied directly to dentition without the use of a tray. Once the material has set, the tray, if used, can be left in place or removed.

FIG. 1 shows a preferred form of packaging for materials according to the present invention. The package 10 of FIG. 1 includes a first syringe 11 connected at its output end 12 to the output end 13 of a second syringe 14. One of the other syringe by or 14 holds the powder component as described above, while the other holds the liquid component. Any method of selectively preventing fluid communication between syringes 11 and 14 is within the scope of the invention. For example, stopcock 20 may be employed. In this way, the materials may be packaged separately, delivered and shelved until needed. When needed, the interiors of syringes 11 and 14 are caused to come into fluid communication, such as by using other wise conventional stopcock 20. Stopcocks such as stopcock 20 are well known in the art and the internal function of stopcock 20 need not be specifically described.

Once the interior of syringe 11 is in fluid communication with the interior of syringe 14, the user manually depresses one then the other plungers 21 of syringes 11 and 14. The contents of each syringe 11 and 14 are thereby caused to alternately flow therebetween, effecting mixing.

When mixing is completed, the syringes are separated with the mixture held in one syringe 11 or 14. That syringe 11 or 14 is then used to dispense the mixture as required. As stated above, dispensing can be into a conventional dental tray (not shown) or directly onto a tooth.

General Experimental

Formulations according to the present invention were prepared as in Table I. In Table 1, HP is hydrogen peroxide and CP is carbamide peroxide.

TABLE I

| Ingredients | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Solution Phase | | | | | | | | | | | | | | |
| HP 35% | 15 | 24 | 24 | 24 | 25 | 26.7 | 28 | 30 | 30 | 30 | 30 | 30 | 32 | 32 |
| CP 98% | 6 | 6 | 6 | 6 | 10 | 6.7 | 7 | 12 | 12 | 7.5 | 7.5 | 7.5 | 8 | 8 |
| Glycerin | 9 | | | 15 | 15 | 16.8 | 17.5 | 18 | 18 | 18.75 | 18.75 | 18.75 | 20 | |
| Water | 30 | 30 | 30 | 15 | | 16.8 | 17.5 | | | 18.75 | 18.75 | 18.75 | 20 | |
| Powder Phase | | | | | | | | | | | | | | |
| Gantrez MS-955 | 40 | 40 | 39 | 40 | 50 | 33 | 30 | 38.1 | 40 | 23.33 | 24.99 | 25 | 20 | 60 |
| Titanium Dioxide | | | 1 | | | | | 1.9 | | 1.67 | 0.01 | | | |

| Ingredients | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| Solution Phase | | | | | | | | | | | | | | | |
| HP 35% | 33.28 | 36 | 36 | 36.4 | 37 | 37 | 40 | 40.2 | 48 | 48 | 50 | 60 | 64 | 64 | 70 |
| CP 98% | 8.32 | | | 9.1 | | | 10 | 10 | 12 | 12 | | 15 | 16 | 16 | |
| Glycerin | 16.8 | 24 | 24 | 18.1 | 25 | 26 | | | | | | | | | |
| Water | | | | | | | | 16.8 | | | | | | | |
| Powder Phase | | | | | | | | | | | | | | | |
| Gantrez MS-955 | 41.6 | 39 | 40 | 36.4 | 37 | 37 | 50 | 32 | 40 | 38.1 | 50 | 25 | 19 | 20 | 30 |
| Titanium Dioxide | | | 1 | | 1 | | | 0.8 | | 1.9 | | | 1 | | |

Formulations according to Table 1, when prepared according to the description provided above, either with syringes 11, 14, or by some other method of mixing the liquid and powder component, within 1 to 10 minutes will set to a elastomeric-like semi-solid texture that also exhibits a fluid-like characteristic. The Material can then be placed into a dental tray, mouthpiece or other delivery medium for delivery onto tooth surfaces. Because of the presence of the peroxide component or components, the tooth whitening materials will have a tooth whitening effect upon the tooth surfaces, in an otherwise conventional manner. It has been found that the transition from a pourable fluid, upon initial mixing of the liquid and powder components to an elastic semi-solid phase, can be affected by many factors, including for example the rate ratio of the solution (liquid) phase to the powder phase, the moisture content of the powder phase, the temperature of the solution phase and powder phase part to mixing, the mixing technique itself, and the like.

Based upon the foregoing disclosure, it should now be apparent that the tooth whitening composition and method of whitening teeth as described herein will carry out the objects of the invention set forth hereinabove. It is, therefore, to be understood that any obvious variations fall within the scope of the claimed invention and thus, the selection of specific constituents and substituents can be determined without departing from the spirit of the invention herein disclosed and described. Thus, the scope of the invention shall include all modifications and variations that may fall within the scope of the attached claims.

What is claimed is:

1. A tooth whitening composition comprising:

a mixture comprising a powder phase and a liquid phase; said powder phase comprising a salt selected from the group consisting of a mixed powder of sodium/calcium salts of the copolymer of methyl vinyl ether/maleic anhydride, a blend of mixed sodium/calcium salts of the copolymer of methyl vinyl ether/maleic anhydride, and mixtures thereof, and optionally, a filler; said liquid phase comprising a solution of from about 3 to about 50 percent by weight of hydrogen peroxide in water.

* * * * *